US012633391B2

(12) United States Patent
Rhrissorrakrai et al.

(10) Patent No.: US 12,633,391 B2
(45) Date of Patent: May 19, 2026

(54) PHENOTYPE CLASSIFICATION FROM PERSISTENT BETTI CURVE ANALYSIS

(71) Applicant: International Business Machines Corporation, Armonk, NY (US)

(72) Inventors: Kahn Rhrissorrakrai, Middle Village, NY (US); Filippo Utro, Pleasantville, NY (US); Aldo Guzman Saenz, White Plains, NY (US); Laxmi Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 86 days.

(21) Appl. No.: 18/536,325

(22) Filed: Dec. 12, 2023

(65) Prior Publication Data

US 2025/0191727 A1 Jun. 12, 2025

(51) Int. Cl.
*G16H 20/40* (2018.01)
*G16H 15/00* (2018.01)

(52) U.S. Cl.
CPC ............. *G16H 20/40* (2018.01); *G16H 15/00* (2018.01)

(58) Field of Classification Search
CPC .............................. G16H 20/40; G16H 15/00
See application file for complete search history.

(56) References Cited

U.S. PATENT DOCUMENTS

| | | | |
|---|---|---|---|
| 9,430,688 | B1 | 8/2016 | Ray |
| 10,839,258 | B2 | 11/2020 | Todoriki et al. |
| 11,024,022 | B2 | 6/2021 | Umeda et al. |
| 11,120,302 | B2 | 9/2021 | Umeda |
| 11,321,841 | B2 | 5/2022 | Nakane et al. |
| 11,410,055 | B2 | 8/2022 | Tsunoda et al. |
| 2017/0147946 | A1 | 5/2017 | Umeda |
| 2019/0228516 | A1 | 7/2019 | Umeda et al. |
| 2019/0236407 | A1 | 8/2019 | Todoriki et al. |
| 2019/0304568 | A1* | 10/2019 | Wei ......................... G16B 10/00 |
| 2019/0385020 | A1 | 12/2019 | Umeda |

(Continued)

OTHER PUBLICATIONS

J. Youssef et al., A Review of Closed-Loop Algorithms for Glycemic Control in the Treatment of Type 1 Diabetes, 2 Algorithms 518-532 (Mar. 12, 2009) (Year: 2009).*

(Continued)

*Primary Examiner* — Jordan L Jackson
(74) *Attorney, Agent, or Firm* — Cantor Colburn LLP; Kelsey M. Skodje

(57) ABSTRACT

A computer-implemented method for data analysis is provided. The computer-implemented method includes splitting data into first and second training data and first and second test data, partitioning the first and second training data into first and second partitions, generating initial Betti curves for the first and second partitions, training a model to recognize Betti curves of the first and second data types on the initial Betti curves, adding each of the first and second test data to each of the first and second partitions to form new first and second partitions, generating new Betti curves for the new first and second partitions, having the model determine whether each of the first and second test data are likely to be first or second data types from new and initial Betti curve deviations and iteratively re-training the model based on determination accuracies.

14 Claims, 5 Drawing Sheets

(56) References Cited

U.S. PATENT DOCUMENTS

| 2020/0184353 | A1 | 6/2020 | Tsunoda et al. |
| 2020/0372649 | A1 | 11/2020 | Nakane et al. |
| 2020/0397330 | A1 | 12/2020 | Kobayashi et al. |

OTHER PUBLICATIONS

Georgina Gonzalez et al., Prediction in Cancer Genomics Using Topological Signatures and Machine Learning, 15 Topological Data Analysis 247-276 (Jun. 26, 2020) (Year: 2020).*

Ameer Saadat-Yazdi et al., Topological Detection of Alzheimer's Disease Using Betti Curves, Interpretability of Machine Intelligence in Medical Image Computing, and Topological Data Analysis and Its Applications for Medical Data 119-128 (Sep. 21, 2021) (Year: 2021).*

Chazal and Michel, An Introduction to Topological Data Analysis: Fundamental and Practical Aspects for Data Scientists, 4 Frontiers in artificial Intelligence (Sep. 28, 2021) (Year: 2021).*

Aslam et al., "TAaCGH Suite for Detecting Cancer—Specific Copy Number Changes Using Topological Signatures" Entropy 24.7, 896 (2022): pp. 1-30.

Bhaskar et al., "Capturing Spatiotemporal Signaling Patterns in Cellular Data withGeometric Scattering Trajectory Homology," bioRxiv (2023): pp. 1-28.

Masoomy et al. "Topological analysis of interaction patterns in cancer-specific gene regulatory network: Persistent homology approach." Scientific Reports 11.1. 16414 (2021): 11 pages.

Meng, Zhenyu, et al. "Weighted persistent homology for biomolecular data analysis." Scientific reports 10.1 , 2079 (2020): 15 pages.

* cited by examiner

Training data $T$ with phenotypes $P$. Testing data $E$ includes at least 1 sample without a label and identical features to $T$.

Invention includes method to calculate persistent Betti curves $B(I, d)$ given some input data $I$ and specified dimension $d$.

---

Algorithm 1 Betti Phenotype Classifier: Calculate per phenotype assignment scores from Betti values

---

Require: A training matrix $T \in R^{n \times f}$, where $n$ is the number of individuals and $f$ is the number of features; target phenotypes $P \in R^n$; dimensions $D$ to test; test sample vector $E \in R^f$; be $n_S$, the number of representatives wanted and $n_p$ the number of element to be selected for each phenotype to create such representatives.

Ensure: A vector $E_p \in R^P$ representing scores for each phenotype for $E$.

1: for all $p \in P$ do,
2:     for all $it$ in $[1, n_S]$ do
3:         select $n_p$ elements (with/without repetition) in $T$.
4:         for all $d$ in $[0, D]$ do
5:             Generate the $B_{pd}$ using eqn. (1) for the sample set $N_{pd}$
6:         end for
7:     end for
8: end for
9: for all $d$ in $[0, D]$ do
10:     Train a model $M^d$ on the Betti curves created on step 5.
11:     for all $t$ in the test set do,
12:         for all $p$ in $P$ do
13:             Consider $N_{pd} \cup \{t\}$ set, measure the change in performance of $M^d$.
14:         end for
15:     end for
16:     Assign $t$ to the phenotype based on the performance changes in $M^d$
17: end for
18: Construct $E$ on a (weighted) combination of the prediction in steps 16.

---

Equation to calculate the Betti curve for phenotype sample set $N_{pd}$ for dimension $d$.

$$B_{pd} = B(N_{pd}, d) \tag{1}$$

FIG. 5

PHENOTYPE CLASSIFICATION FROM PERSISTENT BETTI CURVE ANALYSIS

BACKGROUND

The present invention generally relates to data analysis in computing systems. More specifically, the present invention relates to phenotype classification from persistent Betti curve analysis.

In genetics, the term "phenotype" refers to a set of observable characteristics or traits of an organism. The term covers the organism's morphology (i.e., its physical form and structure), its developmental processes its biochemical and physiological properties, its behavior and the products of its behavior. An organism's phenotype results from two basic factors: the expression of an organism's genetic code or "genotype" and the influence of environmental factors. Both factors may interact, further affecting the phenotype.

SUMMARY

A computer-implemented method for data analysis is provided. The computer-implemented method includes splitting data into first and second training data and first and second test data, partitioning the first and second training data into first and second partitions, generating initial Betti curves for the first and second partitions, training a model to recognize Betti curves of the first and second data types on the initial Betti curves, adding each of the first and second test data to each of the first and second partitions to form new first and second partitions, generating new Betti curves for the new first and second partitions, having the model determine whether each of the first and second test data are likely to be first or second data types from new and initial Betti curve deviations and iteratively re-training the model based on determination accuracies. In accordance with additional or alternative embodiments, the computer-implemented method provides for scoring patients for disease phenotypes based on the very structure of the data projected into a higher dimensional space using algebraic topology and persistent homology as represented in persistent Betti curves.

A computer program product for data analysis is provided. The computer program product includes one or more computer readable storage media having computer readable program code collectively stored on the one or more computer readable storage media, the computer readable program code being executed by a processor of a computer system to cause the computer system to perform a method. The method includes splitting data into first and second training data and first and second test data, partitioning the first and second training data into first and second partitions, generating initial Betti curves for the first and second partitions, training a model to recognize Betti curves of the first and second data types on the initial Betti curves, adding each of the first and second test data to each of the first and second partitions to form new first and second partitions, generating new Betti curves for the new first and second partitions, having the model determine whether each of the first and second test data are likely to be first or second data types from new and initial Betti curve deviations and iteratively re-training the model based on determination accuracies. In accordance with additional or alternative embodiments, the method provides for scoring patients for disease phenotypes based on the very structure of the data projected into a higher dimensional space using algebraic topology and persistent homology as represented in persistent Betti curves.

A computing system is provided and includes a processor, a memory coupled to the processor and one or more computer readable storage media coupled to the processor. The one or more computer readable storage media collectively contain instructions that are executed by the processor via the memory to implement a method for data analysis. The method includes splitting data into first and second training data and first and second test data, partitioning the first and second training data into first and second partitions, generating initial Betti curves for the first and second partitions, training a model to recognize Betti curves of the first and second data types on the initial Betti curves, adding each of the first and second test data to each of the first and second partitions to form new first and second partitions, generating new Betti curves for the new first and second partitions, having the model determine whether each of the first and second test data are likely to be first or second data types from new and initial Betti curve deviations and iteratively re-training the model based on determination accuracies. In accordance with additional or alternative embodiments, the method provides for scoring patients for disease phenotypes based on the very structure of the data projected into a higher dimensional space using algebraic topology and persistent homology as represented in persistent Betti curves.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 5 is a schematic diagram illustrating an algorithm for executing the computer-implemented method of FIG. 3 in accordance with embodiments.

Figure 1:
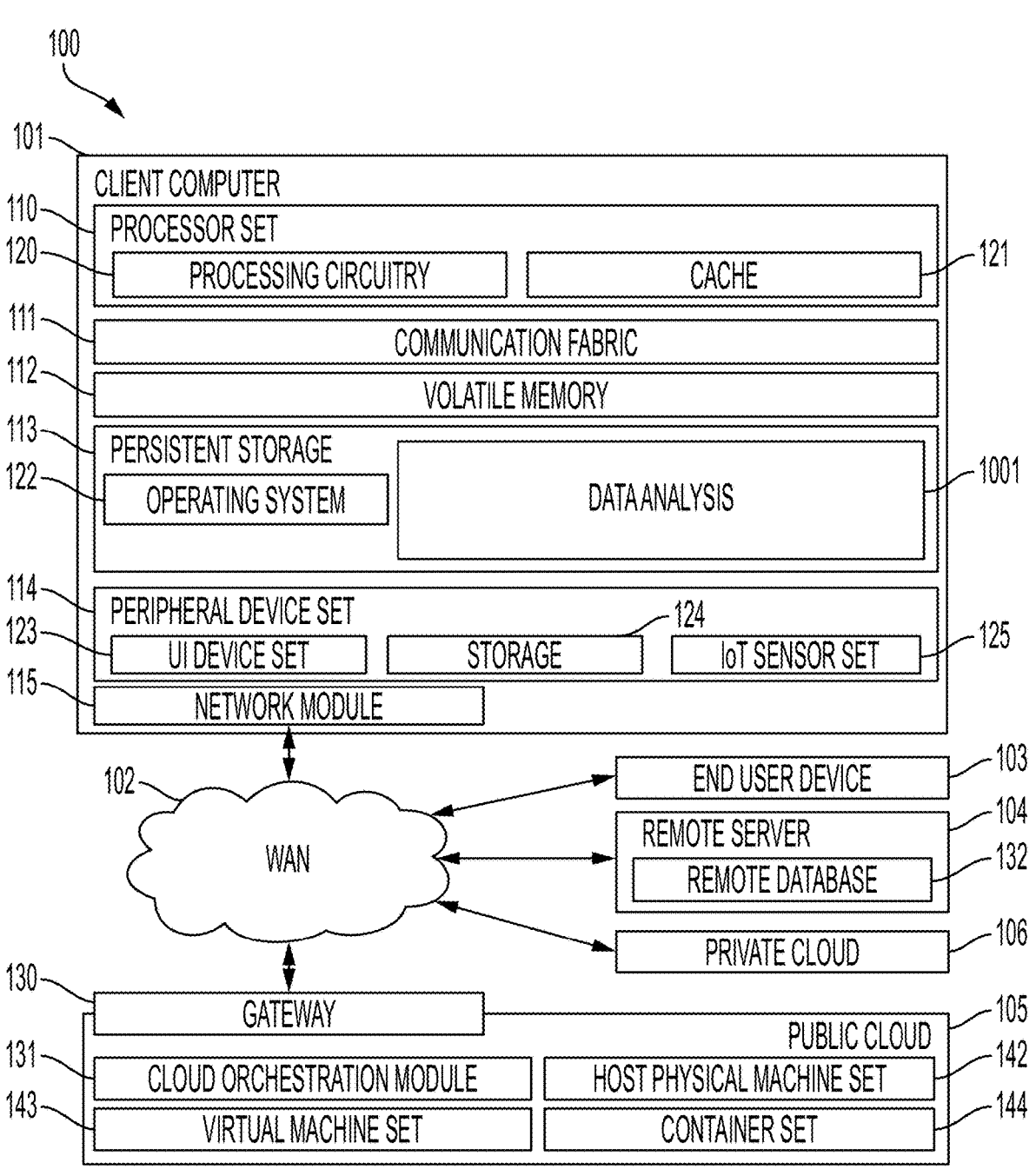
FIG. 1 is a schematic diagram of a computing environment for executing a computer-implemented method for operating a chip handling assembly in accordance with one or more embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two- or three-digit reference numbers. With minor exceptions, the leftmost digit(s) of each reference number correspond to the figure in which its element is first illustrated.

DETAILED DESCRIPTION

A computer-implemented method for data analysis is provided. The computer-implemented method includes splitting data into first and second training data and first and second test data, partitioning the first and second training data into first and second partitions, generating initial Betti curves for the first and second partitions, training a model to recognize Betti curves of the first and second data types on the initial Betti curves, adding each of the first and second test data to each of the first and second partitions to form new first and second partitions, generating new Betti curves for the new first and second partitions, having the model determine whether each of the first and second test data are likely to be first or second data types from new and initial Betti curve deviations and iteratively re-training the model based on determination accuracies. In accordance with additional or alternative embodiments, the computer-implemented method provides for scoring patients for disease phenotypes based on the very structure of the data projected into a higher dimensional space using algebraic topology and persistent homology as represented in persistent Betti curves.

The first data type is associated with a first cancer and the second data type is associated with a second cancer. Thus, the computer-implemented method can be applied to cases in which cancer samples are being studied.

The training can include re-sampling of the data. This allows for the model to be trained and verified as a robust model.

The iteratively re-training of the model can include ignoring a least likely result. This allows for the model to be re-trained in an efficient manner.

In addition, the model can be used to determine whether newly received data is associated with the first or second data types following the iteratively re-training of the model. As such, the model can be employed in diagnostic analysis for patients.

A report can be generated in accordance with the newly received data being determined to be associated with the first or second data types. As such, the model can be used as a tool for health professionals.

A treatment course for a patient from whom the newly received data is drawn can be automatically activated in accordance with the newly received data being determined to be associated with the first or second data types. As such, the model can be used as an automated tool for health professionals, especially in a busy environment.

A computer program product for data analysis is provided. The computer program product includes one or more computer readable storage media having computer readable program code collectively stored on the one or more computer readable storage media, the computer readable program code being executed by a processor of a computer system to cause the computer system to perform a method. The method includes splitting data into first and second training data and first and second test data, partitioning the first and second training data into first and second partitions, generating initial Betti curves for the first and second partitions, training a model to recognize Betti curves of the first and second data types on the initial Betti curves, adding each of the first and second test data to each of the first and second partitions to form new first and second partitions, generating new Betti curves for the new first and second partitions, having the model determine whether each of the first and second test data are likely to be first or second data types from new and initial Betti curve deviations and iteratively re-training the model based on determination accuracies. In accordance with additional or alternative embodiments, the method provides for scoring patients for disease phenotypes based on the very structure of the data projected into a higher dimensional space using algebraic topology and persistent homology as represented in persistent Betti curves.

The first data type is associated with a first cancer and the second data type is associated with a second cancer. Thus, the method can be applied to cases in which cancer samples are being studied.

The training can include re-sampling of the data. This allows for the model to be trained and verified as a robust model.

The iteratively re-training of the model can include ignoring a least likely result. This allows for the model to be re-trained in an efficient manner.

In addition, the model can be used to determine whether newly received data is associated with the first or second data types following the iteratively re-training of the model. As such, the model can be employed in diagnostic analysis for patients.

A report can be generated in accordance with the newly received data being determined to be associated with the first or second data types. As such, the model can be used as a tool for health professionals.

A treatment course for a patient from whom the newly received data is drawn can be automatically activated in accordance with the newly received data being determined to be associated with the first or second data types. As such, the model can be used as an automated tool for health professionals, especially in a busy environment.

A computing system is provided and includes a processor, a memory coupled to the processor and one or more computer readable storage media coupled to the processor. The one or more computer readable storage media collectively contain instructions that are executed by the processor via the memory to implement a method for data analysis. The method includes splitting data into first and second training data and first and second test data, partitioning the first and second training data into first and second partitions, generating initial Betti curves for the first and second partitions, training a model to recognize Betti curves of the first and second data types on the initial Betti curves, adding each of the first and second test data to each of the first and second partitions to form new first and second partitions, generating new Betti curves for the new first and second partitions, having the model determine whether each of the first and second test data are likely to be first or second data types from new and initial Betti curve deviations and iteratively re-training the model based on determination accuracies. In accordance with additional or alternative embodiments, the method provides for scoring patients for disease phenotypes based on the very structure of the data projected into a higher dimensional space using algebraic topology and persistent homology as represented in persistent Betti curves.

The first data type is associated with a first cancer and the second data type is associated with a second cancer. Thus, the method can be applied to cases in which cancer samples are being studied.

The training can include re-sampling of the data. This allows for the model to be trained and verified as a robust model.

The iteratively re-training of the model can include ignoring a least likely result. This allows for the model to be re-trained in an efficient manner.

In addition, the model can be used to determine whether newly received data is associated with the first or second data types following the iteratively re-training of the model. As such, the model can be employed in diagnostic analysis for patients.

A report can be generated in accordance with the newly received data being determined to be associated with the first or second data types. As such, the model can be used as a tool for health professionals.

A treatment course for a patient from whom the newly received data is drawn can be automatically activated in accordance with the newly received data being determined to be associated with the first or second data types. As such, the model can be used as an automated tool for health professionals, especially in a busy environment.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

With reference to FIG. 1, a computer or computing device 100 that implements a computer-implemented method for data analysis. The computer or computing device 100 of FIG. 1 contains an example of an environment for the execution of at least some of the computer code involved in performing the inventive methods, such as the block 1001 of the computer-implemented method for data analysis. In addition to the computer-implemented method for data analysis of block 1001, the computer or computing device 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and the computer-implemented method of block 1001, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

The computer 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of the computer-implemented method, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

The processor set 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In the computer-implemented method, at least some of the instructions for performing the inventive methods may be stored in the block 1001 of the computer-implemented method in persistent storage 113.

Communication fabric 111 is the signal conduction path that allows the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

Volatile memory 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

Persistent storage 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface-type operating systems that employ a kernel. The code included in the block 1001 of the computer-implemented method typically includes at least some of the computer code involved in performing the inventive methods.

Peripheral device set 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

Network module 115 is the collection of computer software, hardware, and firmware that allows computer 701 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

End user device (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

Remote server 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

Public cloud 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

Private cloud 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

Turning now to an overview of technologies that are more specifically relevant to aspects of the invention, most diseases and syndromes represent a highly complex set of interactions between different biological entities potentially operating across biological scales, from single cell organisms to entire organ systems. While new phenotypes and patient stratifications can be derived from molecular and electronic health record (EHR) data, as new patients are encountered it is important to be able to assign a form of disease risk score as quickly as possible.

There remains a need for methods and systems that can integrate across multiple data modalities and learn complex features that may only be found in the topological structures of the data yielding unique representations of patient diseases.

Turning now to an overview of the aspects of the invention, one or more embodiments of the invention address the above-described shortcomings of the prior art by providing a computer-implemented method for data analysis. The computer-implemented method for data analysis includes splitting data into first and second training data and first and second test data, partitioning the first and second training data into first and second partitions, generating initial Betti curves for the first and second partitions, training a model to recognize Betti curves of the first and second data types on the initial Betti curves, adding each of the first and second test data to each of the first and second partitions to form new first and second partitions, generating new Betti curves for the new first and second partitions, having the model determine whether each of the first and second test data are first or second data types from new and initial Betti curve deviations and iteratively re-training the model based on determination accuracies.

It is to be understood that the data can be split into more than first and second sets and that there can be more than first and second partitions. The use of first and second data and first and second partitions in this description is for purposes of clarity and brevity and should not be interpreted as limiting in any way.

The above-described aspects of the invention address the shortcomings of the prior art by providing a method for scoring patients for disease phenotypes based on the very structure of the data projected into a higher dimensional space using algebraic topology and persistent homology as represented in persistent Betti curves. That is, the method provides for high-dimensional feature exploitation to diagnose or predict patients for phenotypes of interest. This is a unique application of topological data analysis (TDA) for phenotype prediction and diagnosis. In addition, this uniquely combines a high-dimensional representation of a phenotype using Betti curves and applying a trained model for phenotype prediction on an unlabeled sample. The method naturally integrates multiple types of data, such as multi-omics, imaging, and clinical data leading to identifications of combinatorial features between modalities, such as genomic alteration, clinical data and image features.

Figure 2:
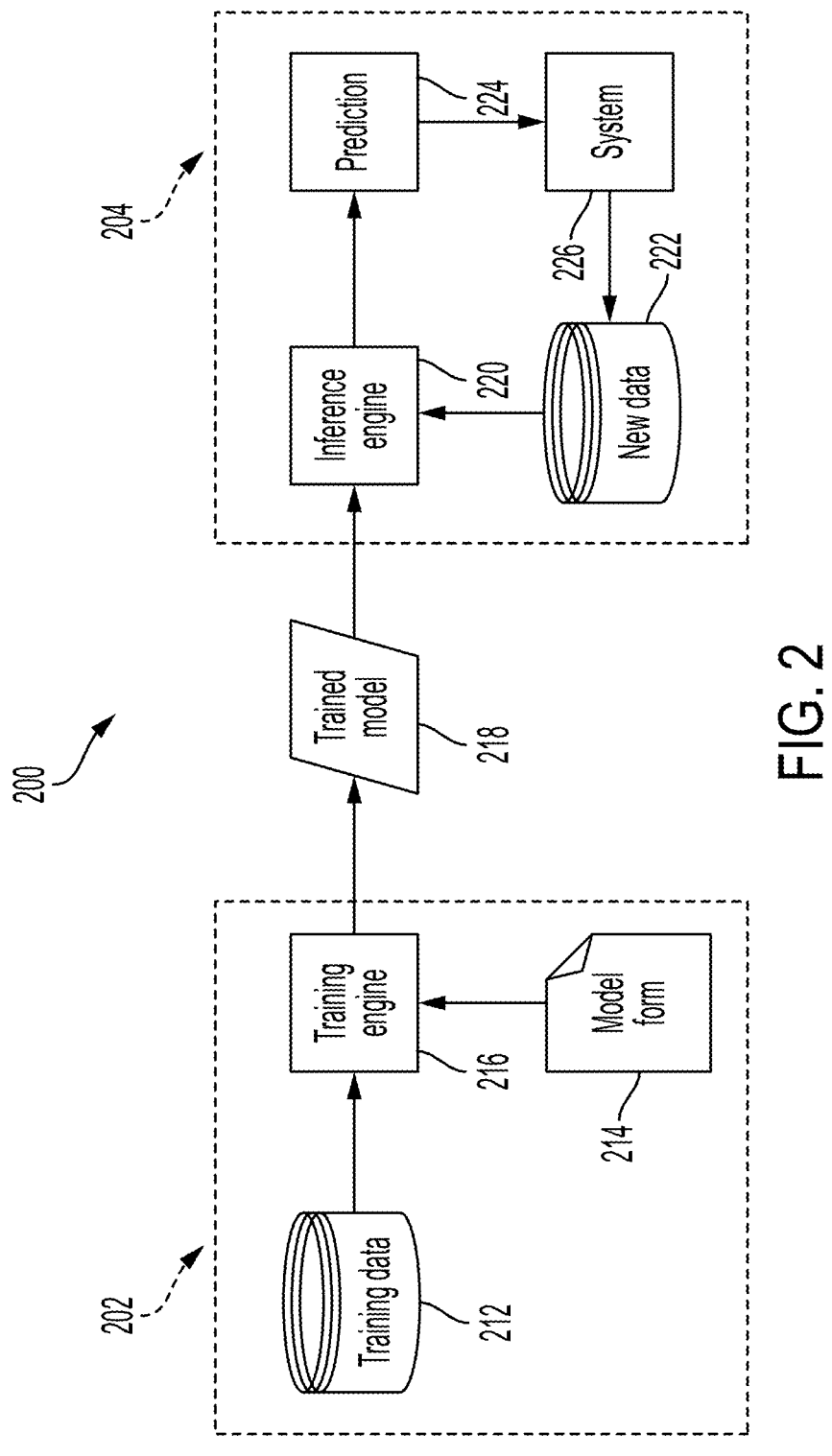
FIG. 2 is a block diagram of components of a machine learning training and inference system according to one or more embodiments of the present invention.

Turning now to a more detailed description of aspects of the present invention, FIG. 2 depicts a block diagram of components of a machine learning training and inference system 200. The machine learning training and inference system 200, in accordance with one or more embodiments of the invention, can utilize machine learning techniques to perform tasks, such as a computer-implemented method for data analysis. Embodiments of the invention utilize AI, which includes a variety of so-called machine learning technologies. The phrase "machine learning" broadly describes a function of electronic systems that learn from data. A machine learning system, engine, or module can include a trainable machine learning algorithm that can be trained, such as in an external cloud environment, to learn functional relationships between inputs and outputs, and the resulting model (sometimes referred to as a "trained neural network," "trained model," and/or "trained machine learning model") can be used for managing information during a web conference, for example. In one or more embodiments of the invention, machine learning functionality can be implemented using an artificial neural network (ANN) having the capability to be trained to perform a function. In machine learning and cognitive science, ANNs are a family of statistical learning models inspired by the biological neural networks of animals, and in particular the brain. ANNs can be used to estimate or approximate systems and functions that depend on a large number of inputs. Convolutional neural networks (CNN) are a class of deep, feedforward ANNs that are particularly useful at tasks such as, but not limited to analyzing visual imagery and natural language processing (NLP). Recurrent neural networks (RNN) are another class of deep, feed-forward ANNs and are particularly useful at tasks such as, but not limited to, unsegmented connected handwriting recognition and speech recognition. Other types of neural networks are also known and can be used in accordance with one or more embodiments of the invention described herein.

ANNs can be embodied as so-called "neuromorphic" systems of interconnected processor elements that act as simulated "neurons" and exchange "messages" between each other in the form of electronic signals. Similar to the so-called "plasticity" of synaptic neurotransmitter connections that carry messages between biological neurons, the connections in ANNs that carry electronic messages between simulated neurons are provided with numeric weights that correspond to the strength or weakness of a given connection. The weights can be adjusted and tuned based on experience, making ANNs adaptive to inputs and capable of learning. For example, an ANN for handwriting recognition is defined by a set of input neurons that can be activated by the pixels of an input image. After being weighted and transformed by a function determined by the network's designer, the activation of these input neurons are then passed to other downstream neurons, which are often referred to as "hidden" neurons. This process is repeated until an output neuron is activated. The activated output neuron determines which character was input. It should be appreciated that these same techniques can be applied in the case of localizing a target object referred by a compositional expression from an image set with similar visual elements as described herein.

The machine learning training and inference system 200 performs training 202 and inference 204. During training 202, a training engine 216 trains a model (e.g., the trained model 218) to perform a task. Inference 204 is the process of implementing the trained model 218 to perform the task in the context of a larger system (e.g., a system 226).

The training 202 begins with training data 212, which can be structured or unstructured data. The training engine 216 receives the training data 212 and a model form 214. The model form 214 represents a base model that is untrained. The model form 214 can have preset weights and biases, which can be adjusted during training. It should be appreciated that the model form 214 can be selected from many different model forms depending on the task to be performed. For example, where the training 202 is to train a model to perform image classification, the model form 214 can be a model form of a CNN (convolutional neural network). The training 202 can be supervised learning, semi-supervised learning, unsupervised learning, reinforcement learning, and/or the like, including combinations and/ or multiples thereof. For example, supervised learning can be used to train a machine learning model to classify an object of interest in an image. To do this, the training data 212 includes labeled images, including images of the object of interest with associated labels (ground truth) and other images that do not include the object of interest with associated labels. In this example, the training engine 216 takes as input a training image from the training data 212, makes a prediction for classifying the image, and compares the prediction to the known label. The training engine 216 then adjusts weights and/or biases of the model based on results of the comparison, such as by using backpropagation. The training 202 can be performed multiple times (referred to as "epochs") until a suitable model is trained (e.g., the trained model 218).

Once trained, the trained model 218 can be used to perform inference 204 to perform a task. The inference engine 220 applies the trained model 218 to new data 222 (e.g., real-world, non-training data). For example, if the trained model 218 is trained to classify images of a particular object, such as a chair, the new data 222 can be an image of a chair that was not part of the training data 212. In this way, the new data 222 represents data to which the model 218 has not been exposed. The inference engine 220 makes a prediction 224 (e.g., a classification of an object in an image of the new data 222) and passes the prediction 224 to the system 226. The system 226 can, based on the prediction 224, taken an action, perform an operation, perform an analysis, and/or the like, including combinations and/or multiples thereof. In some embodiments of the invention, the system 226 can add to and/or modify the new data 222 based on the prediction 224.

In accordance with one or more embodiments of the invention, the predictions 224 generated by the inference engine 220 are periodically monitored and verified to ensure that the inference engine 220 is operating as expected. Based on the verification, additional training 202 can occur using the trained model 218 as the starting point. The additional training 202 can include all or a subset of the original training data 212 and/or new training data 212. In accordance with one or more embodiments of the invention, the training 202 includes updating the trained model 218 to account for changes in expected input data.

Figure 3:
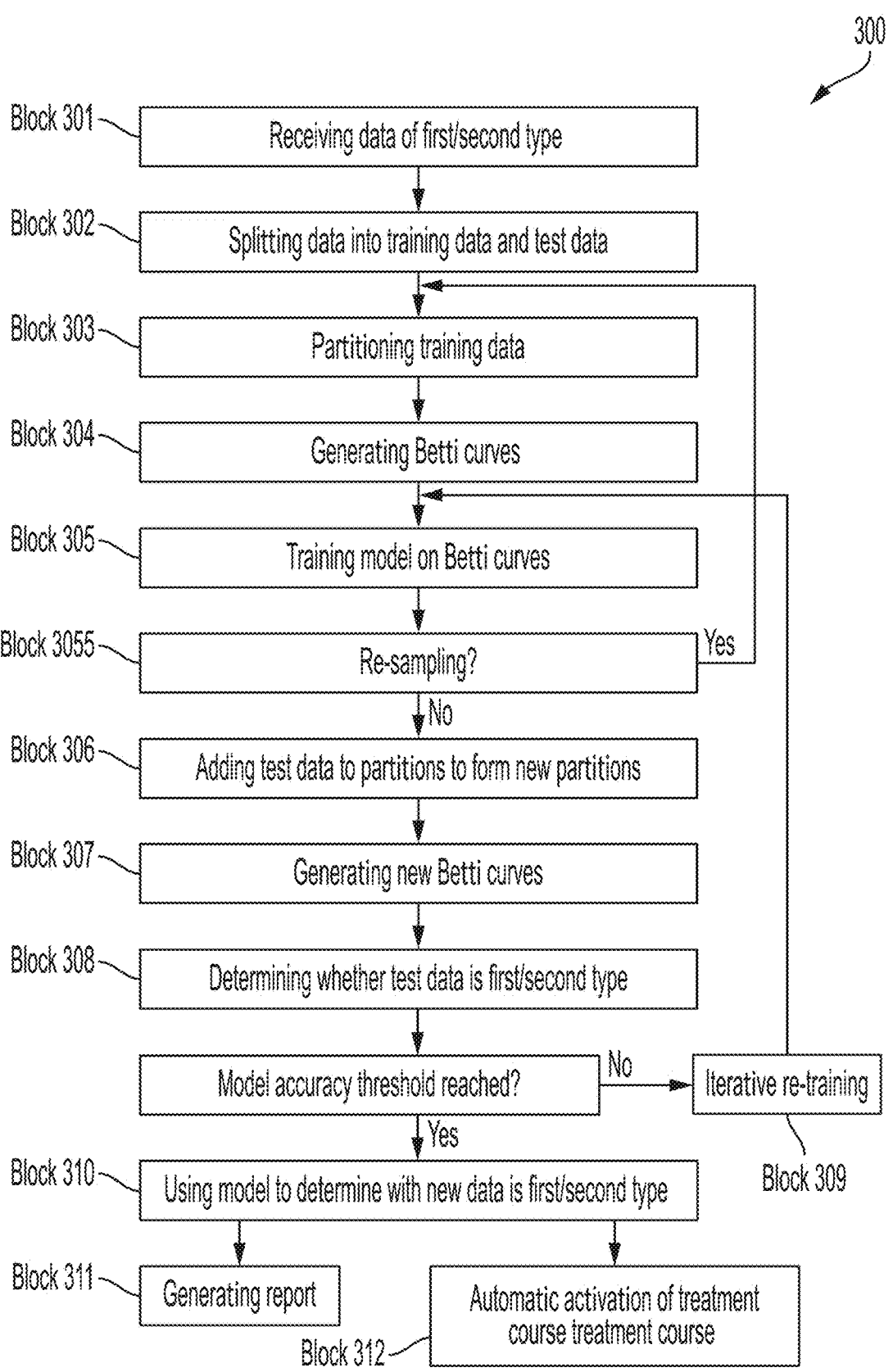
FIG. 3 is a flow diagram illustrating a computer-implemented method for data analysis in accordance with embodiments.

With reference to FIG. 3, a computer-implemented method 300 for data analysis, such as TDA, is provided. As shown in FIG. 3, the computer-implemented method 300 includes receiving data of a first data type and receiving data of a second data type (block 301), splitting the data of the first data type into first training data and first test data and splitting the data of the second data type into second training data and second test data (block 302) and partitioning of the first training data into some number (i.e., three or more) of first training data partitions and partitioning of the second training data into some number (i.e., three or more) of second training data partitions (block 303).

As used herein, the data can be raw data samples relating to characteristics of a first type of cancer, such as breast cancer, and raw data samples relating to characteristics of a second type of cancer, such as lung cancer. Each of the raw data samples can include hundreds, thousands or millions of data points that can be provided as TCGA RNA-Seq data and/or genomic, epigenomic, transcriptomic and proteomic data. The splitting of the data of the first data type into the first training data and the first test data and the splitting of the data of the second data type into the second training data and the second test data of block 302 can result in a 90:10 split between training and test data. The first training data partitions and the second training data partitions can have a same number of data samples in each. Thus, if the data of the first data type is initially received as 100 total data samples and the data of the second data type is initially received as 100 total data samples, as a result of the partitioning of block 303, each of the first training data partitions includes thirty data samples relating to characteristics of breast cancer with ten data samples relating to characteristics of breast cancer reserved for testing and each of the second training data partitions includes thirty data samples relating to characteristics of lung cancer with ten data samples relating to characteristics of lung cancer reserved for testing.

The following description will relate to the case described above for purposes of clarity and brevity.

The computer-implemented method 300 further includes generating initial Betti curves for each of the first training data partitions and for each of the second training data partitions (block 304) and training a model, such as a machine learning (ML) algorithm and/or an artificial intelligence (AI) algorithm, to recognize Betti curves of the first and second data types (i.e., Betti curves of raw data samples relating to characteristics of breast cancer and Betti curves of raw data samples relating to characteristics of lung cancer) on the initial Betti curves (block 305). Since the partitioning of block 303 resulted in three first training data partitions and three second training data partitions, the generating of the initial Betti curves of block 304 results in the generation of three Betti curves of raw data samples relating to characteristics of breast cancer and in the generation of three Betti curves of raw data samples relating to characteristics of breast cancer or six total Betti curves. Further, it will be understood and assumed that the model can be trained on this number of Betti curves.

By way of definition, in algebraic topology, Betti numbers are used to distinguish topological spaces based on connectivity of n-dimensional simplicial complexes. For certain finite-dimensional spaces (such as compact manifolds, finite simplicial complexes or CW complexes), a sequence of Betti numbers is 0 from some point onward (Betti numbers vanish above the dimension of a space), and they are all finite.

In accordance with embodiments, the computer-implemented method 300 can also include a resampling of the data following the training of the model of block 305 (block 3055). In this case, the first training data partitions and the second training data partitions can be discarded and replaced by newly assembled first training data partitions and newly assembled second training data partitions whereupon an additional set of initial Betti curves can be generated. Once the additional set of initial Betti curves are generated, the training of the model of block 305 can be re-executed. Here, instead of the model being trained on six total Betti curves, the model is effectively trained on twelve total Betti curves.

At this point, each data sample of the first and second test data is added to each of the first training data partitions and to each of the second training data partitions to form new first training data partitions of thirty-one data samples and new second training data partitions of thirty-one data samples (block 306) and new Betti curves for each of the new first training data partitions and each of the new second training data partitions are generated (block 307). The model then determines whether each data sample of the first and second test data is likely to be a data sample of a first data type (i.e., a data sample relating to characteristics of breast cancer) or a data sample of a second data type (i.e., a data sample relating to characteristics of lung cancer) from deviations between the new Betti curves and the initial Betti curves (block 308).

The determination of block 308 can be executed by the model reviewing the new Betti curves and the initial Betti curves, identifying the deviations between the new Betti curves and the initial Betti curves and making a quantitative or qualitative judgment about those deviations. For example, for a given data sample, if the new Betti curves of the new second training data partitions differ from the initial Betti curves of the second training data partitions to a greater extent than they differ from the initial Betti curves of the first training data partitions, the model can in some cases judge that the given data sample is likely to not be related to characteristics of lung cancer. Similarly, for a given data sample, if the new Betti curves of the new second training data partitions differ from the initial Betti curves of the second training data partitions to a greater extent than they differ from the initial Betti curves of the first training data partitions, the model can in some cases judge that the given data sample is likely to be related to characteristics of breast cancer.

Following the determination of block 308, the computer-implemented method 300 can include iteratively re-training the model based on determination accuracies (block 309). That is, in the example given above, since the given data sample is known to be related to characteristics of breast cancer or lung cancer, an accuracy of the determination of block 308 by the model can be ascertained once testing is completed for the ten data samples relating to characteristics of breast cancer reserved for testing and for the ten data samples relating to characteristics of lung cancer reserved for testing. In accordance with embodiments, an accuracy threshold can be set (i.e., 80% correct) whereby when the model is found to be less than 80% correct in a given run the model is iteratively re-trained until its accuracy score exceeds the accuracy threshold. At this point, the model can be considered to be a verified model.

In accordance with embodiments, the iteratively re-training of the model of block 309 can include ignoring a least likely result. That is, in an event the training of the model of block 305 made use of six total Betti curves and a determination of block 308 revealed that, for a given data sample of, for example, breast cancer, deviations between one pair of the new Betti curves and the initial Betti curves associated with lung cancer exceeded all the other deviations, that pair can be discarded during re-training of the model to recognize Betti curves for data samples associated with characteristics of breast cancer.

With continued reference to FIG. 3, once the model can be considered to be a verified model, the computer-implemented method 300 can further include using the model to determine whether newly received data (i.e., raw data samples relating to characteristics of an unknown type of cancer) is associated with the first or second data types (block 310) and at least one of generating a report in accordance with the newly received data being determined to be associated with the first or second data types (block 311) for use by a medical professional, for example, and automatically activating a treatment course for a patient from whom the newly received data is drawn in accordance with the newly received data being determined to be associated with the first or second data types (block 312).

Figure 4:
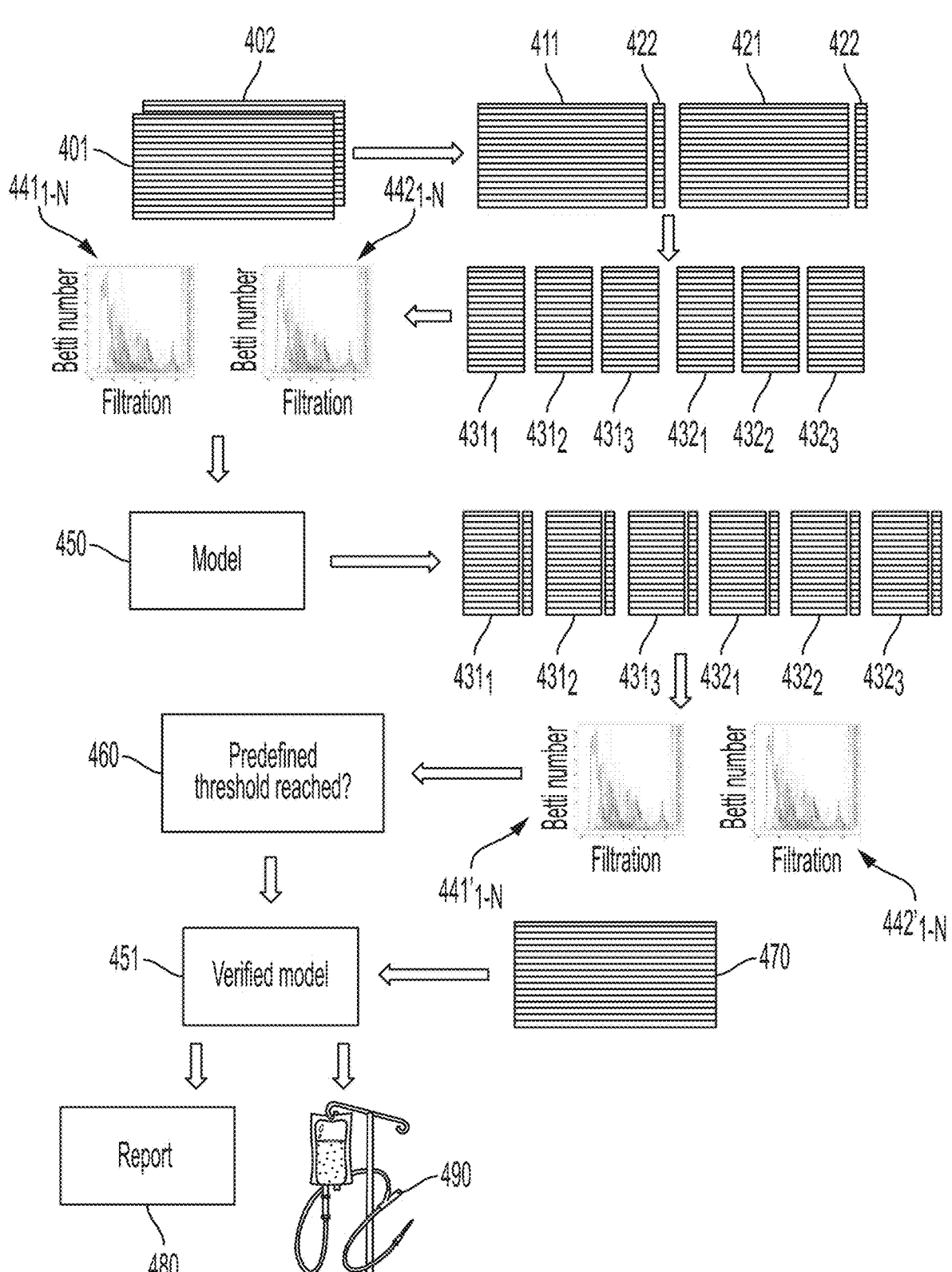
FIG. 4 is a graphical flow diagram illustrating the computer-implemented method for data analysis of FIG. 3 in accordance with embodiments.

If the invention identifies that the patient sample is of a particular subtype of breast cancer known to be responsive to drug A as opposed to drug B, then the invention can automatically activate/recommend that as the most appropriate treatment course. Another case could be if the invention was trained towards classes related to drug response mechanisms and a patient is already under treatment with drug C and during monitoring of therapeutic response, the model identifies that the patient now resembles the non-responsive Betti curve and so can automatically alter/rec-ommend the termination of treatment with drug C. With reference to FIG. 4, an exemplary execution of the com-puter-implemented method 300 of FIG. 3 is illustrated graphically. As shown in FIG. 4, raw data samples 401, 402 relating to breast cancer and lung cancer are received and split into first and second training data 411, 412 and first and second test data 421, 422 whereupon the first and second training data 411, 412 are partitioned into first and second training data partitions $431_{1-N}$, $432_{1-N}$. Initial Betti curves $441_{1-N}$, $442_{1-N}$ for each of the first and second training data partitions $431_{1-N}$, $432_{1-N}$ are then generated. A model 450 is subsequently trained on the initial Betti curves $441_{1-N}$, $442_{1-N}$(with or without re-sampling) so that the model 450 can recognize a Betti curve that is indicative of breast cancer from initial Betti curves $441_{1-N}$ and so that the model 450 can recognize a Betti curve that is indicative of lung cancer from initial Betti curves $442_{1-N}$.

A data sample from the first test data 421 is then added to each of the first and second training data partitions $431_{1-N}$, $432_{1-N}$ to form new first and second training data partitions $431'_{1-N}$, $432'_{1-N}$ and new Betti curves $441'_{1-N}$, $442'_{1-N}$ are generated. The model 450 is then used to determine whether the data sample from the first test data 421 likely relates to characteristics of breast cancer or lung cancer by consider-ing deviations between the initial Betti curves $441_{1-N}$, $442_{1-N}$ and the new Betti curves $441'_{1-N}$, $442'_{1-N}$. Since it is known that the data sample from the first test data 421 relates to characteristics of breast cancer, it can be deter-mined whether the determination by the model 450 is accurate or inaccurate. This process is repeated for each data sample from the first and second test data 421, 422 whereby an accuracy score for the model 450 can be calculated. If the accuracy score exceeds a predefined threshold 460, no re-training is needed and the model 450 can be considered a verified model 451. If the accuracy score does not exceed the predefined threshold 460, re-training may be warranted.

Once the model 450 can be considered to be a verified model, the model 450 can be used to determine whether raw data samples of newly received data 470 relate to charac-teristics of breast cancer or lung cancer by essentially repeating the process described above with the raw data samples replacing the test data to form new partitions. Based on that determination, a report 480 can be generated and/or a treatment course 490 can be automatically activated.

As described above, a supervised ML/AI approach is provided for TDA to score individual patient samples for a phenotype(s) of interest. Using TDA versus conventional methods for phenotype prediction and classification has certain advantages in that it can leverage non-linearities in the data through its structure, is robust to noise and naturally provides dimensional reduction that may lead to improved embeddings for a trained ML/AI model to classify samples.

Input data is split into training data T and test data E whereupon persistent Betti curves B are calculated, where Betti numbers are the number of structures at a given dimension $d \epsilon D$, where $D=Z^+_0$ and persistent Betti curves are Betti numbers over filtration steps. For example, B at d=0; 1; 2 are points, circles and voids, respectively. $B_{pd}$ is learned for each phenotype $p \epsilon P$ (e.g., for cancer sub-type from all cancers in a dataset), where $B_{pd}$ is calculated from a fixed number of samples $N_{pd}$, where any number of $N_{pd}$ are created during the training phase of the invention. In some cases, sub-sampling with repetition can be executed. A size of $N_{pd}$ may be dependent on the size of p. A model $M_d$ is trained for $B_{pd}$ for each de D. $N_{pd}$ can be constructed from samples pre-dominantly but not exclusively drawn from p. In this way $N_{pd}$ captures a noisier space that reflects the heterogeneous nature of certain diseases whose phenotype boundaries are less distinct. During a testing phase, unla-beled sample t with an identical feature space can be added to each $N_{pd}$ to give $N'_{pd}$ and $B_{pd}$ is recalculated as $B'_{pd}$ for each given dimension d. The differences in the prediction performance of model Ma between all $B_{pd}$ and $B'_{pd}$ is then measured. Phenotype scores for E is then a vector of length P where each element captures some value of membership of t to p. It can be then be sorted in ascending order or using a weighted system for each d to represent phenotypes most closely to least closely associated. In some cases, pheno-types for which t is least closely associated are removed from the data. Then, utilizing $N_{pd}$ constructed from samples non-exclusively from p, $B_{pd}$ is recalculated and model Ma is retrained and the testing phase repeated. This can be an iterative elimination process to identify the most closely associated phenotype.

With reference to FIG. 5, an algorithm 500 is provided for the processes described above.

Various embodiments of the present invention are described herein with reference to the related drawings. Alternative embodiments can be devised without departing from the scope of this invention. Although various connec-tions and positional relationships (e.g., over, below, adja-cent, etc.) are set forth between elements in the following description and in the drawings, persons skilled in the art will recognize that many of the positional relationships described herein are orientation-independent when the described functionality is maintained even though the ori-entation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composi-tion, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

Spatially relative terms, e.g., "beneath," "below," "lower," "above," "upper," and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device can be otherwise oriented (rotated 90 degrees or at other orientations) and the spatially relative descriptors used herein interpreted accordingly.

The phrase "selective to," such as, for example, "a first element selective to a second element," means that the first element can be etched and the second element can act as an etch stop.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The term "conformal" (e.g., a conformal layer) means that the thickness of the layer is substantially the same on all surfaces, or that the thickness variation is less than 15% of the nominal thickness of the layer.

The terms "epitaxial growth and/or deposition" and "epitaxially formed and/or grown" mean the growth of a semiconductor material (crystalline material) on a deposition surface of another semiconductor material (crystalline material), in which the semiconductor material being grown (crystalline overlayer) has substantially the same crystalline characteristics as the semiconductor material of the deposition surface (seed material). In an epitaxial deposition process, the chemical reactants provided by the source gases can be controlled and the system parameters can be set so that the depositing atoms arrive at the deposition surface of the semiconductor substrate with sufficient energy to move about on the surface such that the depositing atoms orient themselves to the crystal arrangement of the atoms of the deposition surface. An epitaxially grown semiconductor material can have substantially the same crystalline characteristics as the deposition surface on which the epitaxially grown material is formed. For example, an epitaxially grown semiconductor material deposited on a {100} orientated crystalline surface can take on a {100} orientation. In some embodiments of the invention, epitaxial growth and/or deposition processes can be selective to forming on semiconductor surface, and cannot deposit material on exposed surfaces, such as silicon dioxide or silicon nitride surfaces.

As previously noted herein, for the sake of brevity, conventional techniques related to semiconductor device and integrated circuit (IC) fabrication may or may not be described in detail herein. By way of background, however, a more general description of the semiconductor device fabrication processes that can be utilized in implementing one or more embodiments of the present invention will now be provided. Although specific fabrication operations used in implementing one or more embodiments of the present invention can be individually known, the described combination of operations and/or resulting structures of the present invention are unique. Thus, the unique combination of the operations described in connection with the fabrication of a semiconductor device according to the present invention utilize a variety of individually known physical and chemical processes performed on a semiconductor (e.g., silicon) substrate, some of which are described in the immediately following paragraphs.

In general, the various processes used to form a microchip that will be packaged into an IC fall into four general categories, namely, film deposition, removal/etching, semiconductor doping and patterning/lithography. Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Removal/etching is any process that removes material from the wafer. Examples include etch processes (either wet or dry), and chemical-mechanical planarization (CMP), and the like. Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device. Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for data analysis, the computer-implemented method comprising:

splitting data into first and second training data and first and second test data;

partitioning the first and second training data into first and second partitions;

generating initial Betti curves for the first and second partitions;

training a model to recognize Betti curves of the first and second data types on the initial Betti curves;

modifying the first and second partitions by adding a data sample of each of the first and second test data to each of the first and second partitions to form new first and second partitions;

generating new Betti curves for the new first and second partitions;

having the model identify deviations between the new Betti curves and the initial Betti curves and make a quantitative or qualitative judgment about those deviations to determine whether each of the first and second test data are likely to be first or second data types;

measuring differences in the prediction performance of the model between all initial Betti curves and new initial Betti curves; and setting an accuracy threshold and iteratively re-training the model until its accuracy score exceeds the accuracy threshold, the iteratively re-training including ignoring a least likely result, at which point the model can be considered to be a verified model, wherein the initial Betti curves and the new Betti curves are defined as Betti numbers over filtration steps and the Betti numbers are defined as a number of structures at a given dimension d∈D, where D=Z+0 and the computer-implemented method further comprises:

using the model, following the iteratively re-training of the model, to determine whether newly received data is associated with the first or second data types;

automatically activating a treatment course for a patient from whom the newly received data is drawn in accordance with the newly received data being determined to be associated with the first or second data types; and, in accordance with the newly received data being determined to be associated with the first or second data types, where the training of the model comprises training the model toward classes related to drug response mechanisms and where a patient is already treated with a drug C:

monitoring a therapeutic response of the patient to drug C treatment;

identifying, from results of the monitoring, that the therapeutic response of the patient to the drug C treatment resembles a non-responsive Betti curve; and automatically terminating treatment of the patient with the drug C treatment based on the therapeutic response of the patient to the drug C treatment resembling the non-responsive Betti curve.

2. The computer-implemented method according to claim 1, wherein:

the first data type is associated with a first cancer and the second data type is associated with a second cancer, Betti numbers are defined as the number of structures at a given dimension d∈D, a Betti number Bpd is learned for each phenotype p∈P of the first cancer and the second cancer, where Bpd is calculated from a fixed number of samples Npd, which is dependent on a size of p and which is constructed from samples non-exclusively drawn from p to capture a noisy space reflective of a heterogeneous nature of each of the first cancer and the second cancer, and the training of the model comprises training a model Md for Bpd for each d∈D and testing the model Md during a testing phase, the testing comprising adding an unlabeled sample t with an identical feature space to each Npd to give N'pd and recalculating Bpd as B'pd for each given dimension d.

3. The computer-implemented method according to claim 1, wherein the training comprises re-sampling of the data.

4. The computer-implemented method according to claim 1, wherein the iteratively re-training of the model comprises ignoring a least likely result and, in an event the training of the model uses six total Betti curves and the determining reveals that, for a given data sample of breast cancer, deviations between one pair of the new Betti curves and the initial Betti curves associated with lung cancer exceeded all the other deviations, the computer-implemented method further comprises discarding that one pair during the re-training to recognize Betti curves for data samples associated with characteristics of breast cancer.

5. The computer-implemented method according to claim 1, further comprising generating a report in accordance with the newly received data being determined to be associated with the first or second data types.

6. A computer program product for data analysis, the computer program product comprising one or more computer readable storage media having computer readable program code collectively stored on the one or more computer readable storage media, the computer readable program code being executed by a processor of a computer system to cause the computer system to perform a method comprising:

splitting data into first and second training data and first and second test data;

partitioning the first and second training data into first and second partitions;

generating initial Betti curves for the first and second partitions;

training a model to recognize Betti curves of the first and second data types on the initial Betti curves;

modifying the first and second partitions by adding a data sample of each of the first and second test data to each of the first and second partitions to form new first and second partitions;

generating new Betti curves for the new first and second partitions;

having the model identify deviations between the new Betti curves and the initial Betti curves and make a quantitative or qualitative judgment about those deviations to determine whether each of the first and second test data are likely to be first or second data types;

measuring differences in the prediction performance of the model between all initial Betti curves and new initial Betti curves; and setting an accuracy threshold and iteratively re-training the model until its accuracy score exceeds the accuracy threshold, the iteratively re-training including ignoring a least likely result, at which point the model can be considered to be a verified model, wherein the initial Betti curves and the new Betti curves are defined as Betti numbers over filtration steps and the Betti numbers are defined as a number of structures at a given dimension $d \epsilon D$, where $D=Z+0$ and the computer-implemented method further comprises:

using the model, following the iteratively re-training of the model, to determine whether newly received data is associated with the first or second data types;

automatically activating a treatment course for a patient from whom the newly received data is drawn in accordance with the newly received data being determined to be associated with the first or second data types; and, in accordance with the newly received data being determined to be associated with the first or second data types, where the training of the model comprises training the model toward classes related to drug response mechanisms and where a patient is already treated with a drug C:

monitoring a therapeutic response of the patient to drug C treatment;

identifying, from results of the monitoring, that the therapeutic response of the patient to the drug C treatment resembles a non-responsive Betti curve; and automatically terminating treatment of the patient with the drug C treatment based on the therapeutic response of the patient to the drug C treatment resembling the non-responsive Betti curve.

7. The computer program product according to claim 6, wherein:

the first data type is associated with a first cancer and the second data type is associated with a second cancer, Betti numbers are defined as the number of structures at a given dimension $d \epsilon D$, a Betti number Bpd is learned for each phenotype $p \epsilon P$ of the first cancer and the second cancer, where Bpd is calculated from a fixed number of samples Npd, which is dependent on a size of p and which is constructed from samples non-exclusively drawn from p to capture a noisy space reflective of a heterogeneous nature of each of the first cancer and the second cancer, and the training of the model comprises training a model Md for Bpd for each $d \epsilon D$ and testing the model Md during a testing phase, the testing comprising adding an unlabeled sample t with an identical feature space to each Npd to give N'pd and recalculating Bpd as B'pd for each given dimension d.

8. The computer program product according to claim 6, wherein the training comprises re-sampling of the data.

9. The computer program product according to claim 6, wherein the iteratively re-training of the model comprises ignoring a least likely result and, in an event the training of the model uses six total Betti curves and the determining reveals that, for a given data sample of breast cancer, deviations between one pair of the new Betti curves and the initial Betti curves associated with lung cancer exceeded all the other deviations, the method further comprises discarding that one pair during the re-training to recognize Betti curves for data samples associated with characteristics of breast cancer.

10. The computer program product according to claim 6, wherein the method further comprises generating a report in accordance with the newly received data being determined to be associated with the first or second data types.

11. A computing system comprising:

a processor;

a memory coupled to the processor; and one or more computer readable storage media coupled to the processor, the one or more computer readable storage media collectively containing instructions that are executed by the processor via the memory to implement a method for data analysis comprising:

splitting data into first and second training data and first and second test data;

partitioning the first and second training data into first and second partitions;

generating initial Betti curves for the first and second partitions;

training a model to recognize Betti curves of the first and second data types on the initial Betti curves;

modifying the first and second partitions by adding a data sample of each of the first and second test data to each of the first and second partitions to form new first and second partitions;

generating new Betti curves for the new first and second partitions;

having the model identify deviations between the new Betti curves and the initial Betti curves and make a quantitative or qualitative judgment about those deviations to determine whether each of the first and second test data are likely to be first or second data types;

measuring differences in the prediction performance of the model between all initial Betti curves and new initial Betti curves; and setting an accuracy threshold and iteratively re-training the model until its accuracy score exceeds the accuracy threshold, the iteratively re-training including ignoring a least likely result, at which point the model can be considered to be a verified model, wherein the initial Betti curves and the new Betti curves are defined as Betti numbers over filtration steps and the Betti numbers are defined as a number of structures at a given dimension $d \epsilon D$, where $D=Z+0$ and the computer-implemented method further comprises:

using the model, following the iteratively re-training of the model, to determine whether newly received data is associated with the first or second data types;

automatically activating a treatment course for a patient from whom the newly received data is drawn in accordance with the newly received data being determined to be associated with the first or second data types; and, in accordance with the newly received data being determined to be associated with the first or second data types, where the training of the model comprises training the model toward classes related to drug response mechanisms and where a patient is already treated with a drug C:

monitoring a therapeutic response of the patient to drug C treatment;

identifying, from results of the monitoring, that the therapeutic response of the patient to the drug C treatment resembles a non-responsive Betti curve; and automatically terminating treatment of the patient with the drug C treatment based on the therapeutic response of the patient to the drug C treatment resembling the non-responsive Betti curve.

12. The computing system according to claim 11, wherein:

the first data type is associated with a first cancer and the second data type is associated with a second cancer, Betti numbers are defined as the number of structures at a given dimension d∈D, a Betti number Bpd is learned for each phenotype p∈P of the first cancer and the second cancer, where Bpd is calculated from a fixed number of samples Npd, which is dependent on a size of p and which is constructed from samples non-exclusively drawn from p to capture a noisy space reflective of a heterogeneous nature of each of the first cancer and the second cancer, and the training of the model comprises training a model Md for Bpd for each de D and testing the model Md during a testing phase, the testing comprising adding an unlabeled sample t with an identical feature space to each Npd to give N'pd and recalculating Bpd as B'pd for each given dimension d.

13. The computing system according to claim 11, wherein the training comprises re-sampling of the data.

14. The computing system according to claim 11, wherein the iteratively re-training of the model comprises ignoring a least likely result and, in an event the training of the model uses six total Betti curves and the determining reveals that, for a given data sample of breast cancer, deviations between one pair of the new Betti curves and the initial Betti curves associated with lung cancer exceeded all the other deviations, the method for data analysis further comprises discarding that one pair during the re-training to recognize Betti curves for data samples associated with characteristics of breast cancer.

\* \* \* \* \*